US006534042B2

(12) United States Patent
Delli Santi et al.

(10) Patent No.: US 6,534,042 B2
(45) Date of Patent: *Mar. 18, 2003

(54) TASTE MASKING OF PHENOLICS USING CITRUS FLAVORS

(75) Inventors: Patricia A. Delli Santi, New York, NY (US); Dennis G. A. Nelson, New York, NY (US)

(73) Assignee: Pfizer Inc., Morris Plains, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/033,852

(22) Filed: Dec. 28, 2001

(65) Prior Publication Data

US 2002/0081270 A1 Jun. 27, 2002

Related U.S. Application Data

(60) Continuation of application No. 09/772,682, filed on Jan. 30, 2001, which is a division of application No. 09/298,675, filed on Apr. 23, 1999, now Pat. No. 6,235,267, which is a division of application No. 09/047,741, filed on Mar. 25, 1998, now Pat. No. 5,945,088.
(60) Provisional application No. 60/042,874, filed on Mar. 31, 1997.

(51) Int. Cl.⁷ .............................. A61K 7/16; A61K 7/26
(52) U.S. Cl. ............................................. 424/49; 424/58
(58) Field of Search ...................................... 424/49–58

(56) References Cited

U.S. PATENT DOCUMENTS

| | | | |
|---|---|---|---|
| 3,876,759 A | 4/1975 | Pensak | 424/58 |
| 4,157,401 A | 6/1979 | Stroz | 426/3 |
| 4,332,825 A | 6/1982 | Miyawaki et al. | 426/330.5 |
| 4,412,984 A * | 11/1983 | Van Der Loo et al. | 424/58 |
| 4,420,471 A | 12/1983 | Elton | 424/49 |
| 4,511,488 A | 4/1985 | Matta | 252/162 |
| 4,620,937 A | 11/1986 | Dellutri | 252/143 |
| 4,923,685 A * | 5/1990 | Wuelknitz et al. | 424/54 |
| 4,945,087 A | 7/1990 | Talwar | 514/68 |
| 4,980,152 A * | 12/1990 | Frazier et al. | 424/52 |
| 5,094,843 A | 3/1992 | Mazzobile et al. | 424/52 |
| 5,135,738 A | 8/1992 | Gaffar | 424/49 |
| 5,137,741 A | 8/1992 | Zampino et al. | 426/533 |
| 5,167,951 A | 12/1992 | Gaffar | 424/49 |
| 5,238,915 A | 8/1993 | Fuwa et al. | 512/4 |
| 5,273,741 A | 12/1993 | Gaffar | 424/49 |
| 5,279,813 A | 1/1994 | Gaffar | 424/49 |
| 5,298,238 A | 3/1994 | Gaffar | 424/49 |
| 5,356,615 A | 10/1994 | Gaffar | 424/49 |
| 5,472,685 A | 12/1995 | Gaffar | 424/49 |
| 5,626,837 A * | 5/1997 | Shimada et al. | 424/49 |
| 5,681,548 A | 10/1997 | Esposito et al. | 424/49 |
| 5,723,106 A | 3/1998 | Buch et al. | 424/49 |
| 5,945,088 A * | 8/1999 | Delli Santi et al. | 424/49 |
| 5,965,518 A * | 10/1999 | Nakatsu et al. | 512/1 |
| 6,235,267 B1 * | 5/2001 | Delli Santi et al. | 424/49 |
| 6,261,540 B1 * | 7/2001 | Nelson | 424/53 |

FOREIGN PATENT DOCUMENTS

| | | |
|---|---|---|
| WO | 9407477 | 10/1993 |
| WO | 9416674 | 1/1994 |
| WO | 9418939 | 2/1994 |

OTHER PUBLICATIONS

Yousef, *Chemical Abstracts al* No. 151896b (1979).
Zuckerman, *Nature*, No. 4273, p. 517 (Sep. 22, 1951).

* cited by examiner

*Primary Examiner*—Shep K. Rose
(74) *Attorney, Agent, or Firm*—Darryl C. Little; Evan J. Federman

(57) ABSTRACT

An oral rinse, dentifrice, or oral gel composition comprising:

a) about 0.01 weight % to about 5 weight % of a citrus flavor, citrus flavor ingredient, or mixtures thereof;

b) about 0.01 weight % to about 5 weight % of a phenolic, said phenolic selected from the group consisting of menthol, eucalyptol, methyl salicylate, thymol, triclosan, and mixtures thereof; and c) an orally acceptable carrier.

The claimed composition is useful in retarding the development of plaque, treating gingivitis, and reducing the viable population of micro-organisms in the oral cavity of a mammal.

20 Claims, No Drawings

TASTE MASKING OF PHENOLICS USING CITRUS FLAVORS

This is a continuation of U.S. application Ser. No. 09/772,682 filed Jan. 30, 2001, which, in turn, is a division of U.S. application Ser. No. 09/298,675 filed Apr. 23, 1999, now U.S. Pat. No. 6,235,267, which, in turn, is a division of U.S. application Ser. No. 09/047,741 filed Mar. 25, 1998 which issued as U.S. Pat. No. 5,945,088, which, in turn, claimed priority to U.S. Provisional Application No. 60/042,874 filed Mar. 31, 1997.

This non-provisional application is based upon and claims priority from Provisional Application Ser. No. 60/042,874 filed Mar. 31, 1997.

BACKGROUND OF THE INVENTION

The present invention relates to oral care products comprising citrus-masked phenolics Oral compositions including mouthwashes and dentifrices containing phenolic compounds have been formulated using one or more of the following: menthol, methyl salicylate, eucalyptol and thymol are well known (U.S. Pat. No. 4,945,087, PCT Int. Appl. Nos. WO 94 16,674; WO 94 07,477; WO 94 18,939). These compositions are characterized by their relatively high alcohol levels (20–27 volume %) which causes them to have negative aesthetics, including excessive "bite" and "bum". These compositions often have an unpleasant medicinal taste which can be unattractive to consumers. In particular, thymol is the ingredient which contributes most to the unpleasant, medicinal and harsh taste of these compositions although the combination of several phenolics imparts greater negative taste attributes to these compositions than any one phenolic by itself.

Triclosan (2,4,4'-trichloro-2'-hydroxydiphenyl ether) is a phenolic, nonionic antimicrobial agent used in various soap and toiletry products. In the oral care area, triclosan has been used as a plaque-inhibitory agent in various toothpastes and mouthrinses. Triclosan can have an unpleasant, medicinal taste and at sufficient concentration can cause numbing of the tongue and other mucosal and gingival tissues.

Citrus-flavored mouthwashes or dentifrices have been formulated, as well as methods for preparing clear citrus-flavored mouthwashes including for example, U.S. Pat. Nos. 3,876,759 and 4,420,471.

The use of limonene and its derivatives has been used to improve flavor impact and flavor stability in chewing gum compositions (U.S. Pat. No. 4,157,401) as well as in cleaning compositions (U.S. Pat. Nos. 4,511,488 and 4,620,937). Limonene and its derivatives has been shown to have anti-bacterial effects (Zuckerman, I. "Effect of oxidized d-limonene on micro-organisms" Nature, No. 4273, pp. 517, 1951; Yousef C. A. 91 #151896b (1979), Antimicrobial activity of volatile oil components (limonene)). In the oral care area, limonene has been used as a stabilizer to prevent the loss by adsorption of triclosan on the interior surfaces of packaging containers (U.S. Pat. Nos. 5,187,951; 5,135,738; 5,279,813; 5,273,741).

SUMMARY OF INVENTION

The present invention relates to an oral rinse, dentifrice, or oral gel composition comprising:
a) about 0.01 weight % to about 5 weight % of citrus flavor, citrus flavor ingredient, or mixtures thereof;
b) about 0.01 weight % to about 5 weight % of a phenolic, said phenolic selected from the group consisting of menthol, eucalyptol, methyl salicylate, thymol, triclosan, and mixtures thereof; and
C) an orally acceptable carrier.

A preferred embodiment of the present invention relates to an oral rinse, dentifrice, or oral get composition comprising:
a) about 0.01 weight % to about 5 weight % of a citrus flavor, citrus flavor ingredient, or mixtures thereof;
b) about 0.01 weight % to about 5 weight % of a phenolic, said phenolic selected from the group consisting of menthol, eucalyptol, methyl salicylate, thymol, triclosan, and mixtures thereof;
c) about 0.1 weight % to about 70% of a polyol, said polyol selected from the group consisting of glycerol, sorbitol, propylene glycol, butylene glycol, xylitol, cyclodextrin and its derivatives, and mixtures thereof;
d) about 0.01 weight % to about 10 weight % of an oral acceptable surfactant; and
e) an orally acceptable carrier.

A more preferred embodiment of the present invention relates to an oral rinse, dentifrice, or oral gel composition comprising:
a) about 0.01 weight % to about 5 weight % of citrus flavor selected from the group consisting of orange, grapefruit, lemon, mandarin orange, lime, tangerine, and tangelo; citrus flavor ingredient selected from the group consisting of limonene, citral, cadiene, decylaldehyde, linalool, terpineol, linalyl esters, terpinyl acetate, citronellal, α-terpinene, γ-terpinene, 2-dodecanal, α-pinene, β-pinene, 2-pentenal, decanal, and $C_8$ to $C_{10}$ and $C_{12}$ aldehydes, acids, and esters found in citrus flavors; and mixtures thereof;
b) about 0.01 weight % to about 5 weight % of a phenolic, said phenolic selected from the group consisting of menthol, eucalyptol, methyl salicylate, thymol, triclosan, and mixtures thereof;
c) about 0.1 weight % to about 70% of a polyol, said polyol selected from the group consisting of glycerol, sorbitol, propylene glycol, butylene glycol, xylitol, cyclodextrin and its derivatives, and mixtures thereof;
d) about 0.01 weight % to about 10 weight % of an oral acceptable surfactant; and
e) an orally acceptable carrier.

The present invention also relates to a method for retarding development of plaque on a dental surface in the oral cavity of a mammal, comprising administering to said dental surface an amount of said oral rinse, dentifrice, or oral get composition effective in retarding said development of plaque.

The present invention also relates to a method of treating gingivitis, comprising administering to a mammal in need of such treatment an amount of said oral rinse, dentifrice, or oral gel composition effective in treating gingivitis.

The present invention also relates to a method of treating the presence of microorganisms in the oral cavity of a mammal, comprising administering to the mammal in need of such treatment an amount of said oral rinse, dentifrice, or oral gel composition effective in reducing the viable population of said micro-organisms.

DETAILED DESCRIPTION OF THE INVENTION

The dental formulations in this invention comprise oral rinses (e.g. mouthrinses or washes), dentifrices, and oral gels having an effective concentration of phenolic compounds where the unpleasant taste of the phenolics is masked by the addition of citrus flavor oils, aromatics, oleo resins, extracts, or ingredients thereof.

Citrus flavors that may be employed in this invention include natural and synthetic citrus oils, for example, orange, grapefruit, lemon, mandarin orange, lime, Mexican lime, tangerine, tangelo and blends thereof, as well as citrus aromatics, natural oleo resins, and extracts. Examples of products with synthetic flavors include Carrubba A9047 (an orange flavor) and Noville AN110099 (a citrus mint flavor). These flavors typically contain one or more citrus flavor ingredients including, for example, the following: d-limonene, l-limonene, dl-limonene, alpha-citral and beta-citral (geranol), $\alpha$-terpinene, $\gamma$-terpinene, 2-dodecanal, $\alpha$-pinene, $\beta$-pinene, 2-pentenal, cadiene, decylaldehyde, linalool, terpineol, linalyl esters, terpinyl acetate, citronellal, decanal, as well as $C_8$ to $C_{10}$ and $C_{12}$ aldehydes, acids, and esters found in citrus flavors, and mixtures thereof. Either the natural or synthetic form of these ingredients could be used in the composition of the present invention. Certain of these ingredients may provide a better masking effect of the phenolics in these compositions either alone or in combination with other citrus oil components. For example, terpenes found in citrus flavors may be particularly effective in masking the unpleasant phenolic taste found in these compositions. Limonene is the most abundant terpene in citrus flavor and can be found at levels of approximately 90–95% in citrus flavors. It is possible that this terpene could be an important contributor to the masking effect of unpleasant phenolics by citrus oils. One hypothetical mechanism for the masking ability of citrus oils is that the chemical structure of d-limonene and its isomers is similar to several of the phenolics (e.g. thymol, menthol and eucalytol). Thus, limonene may act as an antagonist to phenolic compounds for taste receptors on the tongue.

Phenolics useful in the present invention include menthol, methyl salicylate, eucalyptol, thymol and triclosan, all of which have an antimicrobial activity. Thymol and triclosan are generally considered to have the best antimicrobial activity. Thymol is also an anthelmintic and an antiseptic. For oral rinses of the present invention, phenolics can be employed at concentrations of from about 0.01 weight % to about 0.5 weight %, preferably about 0.05 weight % to about 0.3 weight % of phenolic compounds selected from a group consisting of menthol, eucalyptol, methyl salicylate, thymol, triclosan, and mixtures thereof. For dentifrices and oral gels of the present invention, the aforementioned phenolic compounds can be useful at concentrations of from about 0.05 weight % to about 5 weight %, preferably about 0.25 weight % to about 3 weight %. The ratio of limonene to phenolic is preferably at least about 0.05:1.

Humectants in dental products of the present invention impart to the mouth a moist and elegant feel and, if incorporated at sufficient concentration, may further inhibit the harshness of the phenolics in these compositions. Some humectants, for example, can provide sweetness to the composition, as well. Suitable humectants include edible polyhydric alcohols such as glycerin, sorbitol, propylene glycol, butylene glycol, xylitol and cyclodextrins, including their derivatives. A humectant generally is present in an amount ranging from about 0.1 weight % to about 30 weight % for oral rinses and from about 10 weight % to about 50 weight % for dentifrice and oral gel compositions.

Oral surfactants useful in the present invention include certain nonionic, anionic and amphoteric surfactants. The preferred oral surfactants include block co-polymers of polyoxyethylene and polyoxypropylene such as the Pluronics from BASF. Other oral surfactants include soluble alkyl sulfonates having 10 to 18 carbon atoms and sulfates of monoglycerides of fatty acids having 10 to 18 carbon atoms or sarcosinates (including salts and derivatives) such as sodium-N-lauroyl sarcosinate. Amphoteric surfactants that can be used include betaines, sulfobetaines and amidobetaines such as the TEGO betaines from Goldschmidt Chemical Corporation. Mixtures of anionic, nonionic and amphoteric surfactants can, be used. These ingredients are generally present from about 0.01 weight % to about 10 weight %, preferably from about 0.01 weight % to 1 weight % for oral rinses and from about 0.5 weight % to about 2 weight % for dentifrices and oral gels.

The orally acceptable carrier of the invention generally includes mixtures of water and ethanol for oral rinses, although the carrier can be alcohol-free, especially in dentifrices and oral gels. For oral rinses, the amount of water can range up to about 25 weight %. The amount of alcohol for oral rinses ranges from about 0 weight % to about 25 weight %, preferably from about 0 weight % to about 15 weight %. For oral gels and dentifrices, the amount of water ranges from about 0 weight % to about 60 weight %, preferably from about 0 wt % to about 40 weight %.

The oral rinse compositions are usually stable so as to be substantially clear and substantially free of precipitation, flocculation, or crystal formation at about room temperature (about 25° C. ) as well as at low temperatures of at least about 5° C. for at least about 1 week. The low temperature stability of these compositions is determined by cooling the compositions to about 5° C., storing for at least seven days and determining whether any precipitate, crystallized or flocculated material is formed in the clear compositions (solutions and oral gels).

For dentifrice and oral gel compositions, abrasives may also be added. Suitable abrasives include precipitated silica or silica gels which have an average particle size ranging from about 0.1 to about 50 microns. Preferred silica abrasives include those marketed under the tradename "Sylodent" or "Syloid" by the W. R. Grace & Co. and those marketed under the tradename "Zeodent" by the J. M. Huber Corp. Other suitable abrasives, having a suitable particle size as described above, include $\beta$-phase calcium pyrophosphate, alumina and calcium carbonate. The amount of abrasive in a dentifrice composition ranges up to about 60 weight %, preferably from about 10 weight % to about 40 weight %.

Oral rinse, dentifrice, and oral gel compositions of the present invention may also contain a suitable fluoride source. Typical sources include soluble salts of the fluoride ion (e g. sodium fluoride, potassium fluoride, stannous fluoride, stannous fluorozirconate) or, soluble salts of the monofluorophosphate ion (e.g. sodium monofluorophosphate). The preferred fluoride source is sodium fluoride. The fluoride ion source should provide from about 50 ppm to about 2,500 ppm fluoride, preferably from about 250 ppm to about 1500 ppm for dentifrice and oral gel compositions, and from about 50 ppm to about 250 ppm fluoride for oral rinses.

Antiplaque agents can also be optionally added to the compositions of the present invention. These include cetyl pyridinium chloride and related quaternary salts such as chlorhexidine, zinc salts such as zinc chloride, stannous salts such as stannous chloride, or stannous fluoride and peroxygens such as hydrogen peroxide, carbamide peroxide, sodium percarbonate, magnesium perphthalate or sodium perborate. These optional antiplaque agents are generally present at levels ranging from about 0 weight % to about 5 weight %.

Anticalculus agents can also be optionally added to the compositions of the present invention. These include tetra-alkali metal pyrophosphate salts and zinc salts, such as zinc chloride. These optional anticalculus agents are generally present at levels ranging from about 0 weight % to about 5 weight % for pyrophosphate salts and from about 0 weight % to about 3 weight % for zinc salts.

In compositions of the present invention, preservatives may be used, especially in non-alcohol or low alcohol compositions. These include benzoic acid, sodium benzoate, methylparaben, propylparaben, sorbic acid and potassium sorbate. These preservative agents are generally present at levels ranging from about 0 weight % to about 2 weight %.

In compositions relating to the invention, buffering systems may be used to stabilize the pH in the product. The pH of the oral rinse, dentifrice, and oral gel compositions can range from about 3.5 to about 8.5. Typical buffering systems include, but are not limited to, citrate, benzoate, gluconate and phosphate. Buffering systems are present in concentrations from about 0.01 weight % to about 1 weight %.

Thickening agents or binders are an optional component of the compositions. Typical thickening include, xanthan gum, carragenan, carboxyvinyl polymers, carbomers, cellulose gums such as carboxymethyl cellulose, cellulose derivatives such as hydroxyethylcellulose and silicas. Thickeners are usually present in the compositions from about 0 weight % to 2 weight % in oral rinses, in which xanthan gum is the preferred thickener. In dentifrices and oral gels, silica-based thickeners can be used at concentrations from about 0 weight % to about 20 weight %. "Sylox" or "Sylodent" by W. R. Grace & Co. are the tradename of the preferred silica-based thickener.

Orally acceptable sweetening agents such as saccharin, lactose, maltose, aspartame, sodium cyclamate, and polydextrose can be added to the compositions. Sweetening agents generally are present in an amount ranging from about 0.001 to about 5 weight % for oral rinse, dentifrice and oral gel compositions. Orally acceptable coloring agents generally are present in an amount ranging from about 0 weight % to about 0.01 weight %.

EXAMPLE 1

The following dental rinse was formulated: Sodium citrate, citric acid, sodium saccharin, sorbitol solution 70% and dye were dissolved in water, at room temperature (which is generally between about 20 and 25° C.), using a mixer with high-lift blade rotating at approximately 200–300 rpm to give a clear aqueous solution. Poloxamer 407, benzoic acid, menthol, thymol, methyl salicylate, eucalyptol and d-limonene were added to the 190° alcohol to give a clear alcoholic solution. The alcoholic phase was added slowly to the aqueous phase which was continually agitated until the addition was complete. The resulting orange product was mixed for a further 30 minutes. The solution had a pH of approximately 4.0.

| INGREDIENT | WEIGHT PERCENT |
| --- | --- |
| Sodium Saccharin | 0.0500 |
| Sodium Citrate | 0.0400 |
| Citric Acid | 0.0100 |
| Sorbitol Solution 70% | 22.0000 |
| FD&C Red No. 40 | 0.0008 |
| D&C Yellow No. 10 | 0.0002 |
| Poloxamer 407 | 0.5000 |
| Alcohol 190 Proof | 17.9000 |
| Benzoic acid | 0.1500 |
| Thymol | 0.0640 |
| Eucalyptol | 0.0920 |
| Menthol | 0.0420 |
| Methyl Salicylate | 0.0600 |
| d-Limonene | 0.1000 |
| Purified Water | 58.9910 |
| Total | 100.0000 |

EXAMPLE 2

The following dental rinse was formulated: Sodium citrate, citric acid, sodium saccharin, sorbitol solution 70%, hydroxypropyl β-cyclodextrin and dyes were dissolved in water, at room temperature, using a mixer with high-lift blade rotating at approximately 200–300 rpm to give a clear aqueous solution. Poloxamer 407, benzoic acid, menthol, thymol, methyl salicylate, eucalyptol and flavor were added to the 190° alcohol to give a clear alcoholic solution. The alcoholic phase was added slowly to the aqueous phase which was continually agitated until the addition was complete. The resulting orange product was mixed for a further 30 minutes. The solution had a pH of approximately 4.0.

| INGREDIENT | WEIGHT PERCENT |
| --- | --- |
| Sodium Saccharin | 0.0500 |
| Sodium Citrate | 0.0400 |
| Citric Acid | 0.0100 |
| Sorbitol Solution 70% | 22.0000 |
| FD&C Red No. 40 | 0.0008 |
| D&C Yellow No. 10 | 0.0002 |
| Hydroxypropyl β-Cyclodextrin | 1.0000 |
| Alcohol 190 Proof | 12.0000 |
| Poloxamer 407 | 0.5000 |
| Benzoic Acid | 0.1500 |
| Thymol | 0.0640 |
| Eucalyptol | 0.0920 |
| Menthol | 0.0420 |
| Methyl Salicylate | 0.0600 |
| Citrus Mint Flavor (Noville AN110099) | 0.1000 |
| Purified Water | 63.8910 |
| Total | 100.0000 |

EXAMPLE 3

The following dental rinse was formulated: Sodium citrate, citric acid, sodium saccharin, sorbitol solution 70%, sodium lauryl sulfate and dye were dissolved in water using a mixer with high-lift blade rotating at approximately 200–300 rpm to give a clear aqueous solution Poloxamer 407, benzoic acid, triclosan (Irgacare MP-Ciba Geigy) and flavor were added to the 190° alcohol to give a clear alcoholic solution. The alcoholic phase was added slowly to the aqueous phase which was continually agitated until the addition was complete. The resulting orange product was mixed for a further 30 minutes. The solution had a pH of approximately 4.0.

| INGREDIENT | WEIGHT PERCENT |
|---|---|
| Sodium Saccharin | 0.0500 |
| Sodium Citrate | 0.0400 |
| Citric Acid | 0.0100 |
| Sorbitol Solution 70% | 22.0000 |
| FD&C Red No. 40 | 0.0003 |
| D&C Yellow No. 10 | 0.0009 |
| Sodium Lauryl Sulfate | 0.2500 |
| Poloxamer 407 | 0.5000 |
| Alcohol 190 Proof | 8.0000 |
| Benzoic Acid | 0.1500 |
| Triclosan | 0.1000 |
| Orange Flavor (Carrubba A9047) | 0.1000 |
| Purified Water | 68.7988 |
| Total | 100.0000 |

EXAMPLE 4

A oral gel dentifrice was formulated by dispersing the carboxymethyl cellulose in the glycerin and polyethylene glycol using a Hobart mixer. The NaF was dissolved separately in the water. The remainder of the water and sorbitol were added to the NaF/water solution and mixed for 25 minutes. Sodium saccharin and hydroxypropyl β-cyclodextrin were then added and mixed for another 10 minutes. Separately the phenolics were mixed together, i.e. eucalyptol, methyl salicylate, thymol and menthol, to make a phenolic phase and the flavor was added to the phenolic phase. The Sylodent 750, Sylodent 15, and dyes were added to the cellulose/sorbitol/cyclodextrin/water phase. Then the phenolic phase, sodium lauryl sulfate and xantham gum were added and mixed thoroughly for 30 minutes. The resulting opacified orange oral gel was deaerated to remove air bubbles.

| INGREDIENT | WEIGHT PERCENT |
|---|---|
| Xanthan Gum | 0.300 |
| Glycerin | 14.000 |
| Sorbitol Solution 70% | 21.171 |
| Carboxymethyl Cellulose, 9M8 | 1.000 |
| Polyethylene Glycol, PEG-8 | 3.000 |
| Purified Water | 14.000 |
| FD&C Red No. 40 | 0.003 |
| D&C Yellow No. 10 | 0.003 |
| Hydroxypropyl β-Cyclodextrin | 15.000 |
| Sodium Saccharin | 0.500 |
| NaF | 0.243 |
| Sylodent 750 | 12.000 |
| Sylodent 15 | 10.000 |
| Thymol | 0.640 |
| Eucalyptol | 0.920 |
| Menthol | 0.420 |
| Methyl Salicylate | 0.600 |
| Sodium Lauryl Sulfate 30% | 5.000 |
| Orange Flavor (Carrubba A9047) | 1.200 |
| Total | 100.000 |

What is claimed is:

1. An oral gel composition comprising:
   a) about 0.01 weight % to about 5 weight % of a citrus flavor, citrus flavor ingredient, or mixtures thereof;
   b) about 0.01 weight % to about 5 weight % of a phenolic, said phenolic selected from the group consisting of menthol, eucalyptol, methyl salicylate, thymol, and mixtures thereof and
   c) an orally acceptable carrier,
   wherein the unpleasant taste of the phenolic is masked by the citrus flavor, citrus flavor ingredient, or mixtures thereof as the essential phenolic taste masking agent to act as an antagonist to phenolic taste receptors on the tongue, said composition being low temperature stable and substantially clear and substantially free of precipitants, flocculants, or crystals at about room temperature.

2. The composition of claim 1, wherein said citrus flavor is selected from the group consisting of orange, grapefruit, lemon, mandarin orange, lime, tangerine, and tangelo; and said citrus flavor ingredient is selected from the group consisting of limonene, citral, cadiene, decylaldehyde, linalool, terpineol, linalyl esters, terpinyl acetate, citronellal, α-terpinene, γ-terpinene, 2-dodecanal, α-pinene, β-pinene, 2-pentenal, decanal, and $C_8$ to $C_{10}$ and $C_{12}$ aldehydes, acids, and esters found in citrus flavors.

3. The composition of claim 1, wherein said citrus flavor, citrus flavor ingredient, or mixtures thereof includes limonene.

4. The composition of claim 3, wherein the ratio of said limonene to said phenolic is at least about 0.05:1.

5. The composition of claim 1, further including about 0.1 weight % to about 70% of a polyol, said polyol selected from the group consisting of glycerol, sorbitol, propylene glycol, butylene glycol, xylitol, cyclodextrin and its derivatives, and mixtures thereof.

6. The composition of claim 1, further including about 0.01 weight % to about 10 weight % of an oral acceptable surfactant.

7. An oral gel composition comprising:
   a) about 0.01 weight % to about 5 weight % of a citrus flavor, citrus flavor ingredient, or mixtures thereof
   b) about 0.01 weight % to about 5 weight % of a phenolic, said phenolic selected from the group consisting of menthol, eucalyptol, methyl salicylate, thymol, and mixtures thereof; and
   c) an orally acceptable carrier,
   wherein said citrus flavor, citrus flavor ingredient, or mixtures thereof includes limonene, and the ratio of said limonene to said phenolic is at least about 0.05:1, and wherein the unpleasant taste of the phenolic is masked by the citrus flavor, citrus flavor ingredient, or mixtures thereof as the essential phenolic taste masking agent to act as an antagonist to phenolic taste receptors on the tongue, said composition being low temperature stable and substantially clear and substantially free of precipitants, flocculants, or crystals at about room temperature.

8. The composition of claim 7, further including about 0.1 weight % to about 70% of a polyol, said polyol selected from the group consisting of glycerol, sorbitol, propylene glycol, butylene glycol, xylitol, cyclodextrin and its derivatives, and mixtures thereof.

9. The composition of claim 7, further including about 0.01 weight % to about 10 weight % of an oral acceptable surfactant.

10. The composition of claim 7, wherein said citrus flavor is selected from the group consisting of orange, grapefruit, lemon, mandarin orange, lime, tangerine, and tangelo.

11. An oral gel composition comprising:
   a) about 0.01 weight % to about 5 weight % of a citrus flavor, citrus flavor ingredient, or mixtures thereof;
   b) about 0.01 weight % to about 5 weight % of a phenolic, said phenolic selected from the group consisting of menthol, eucalyptol, methyl salicylate, thymol, and mixtures thereof;

c) about 0.1 weight % to about 70% of a polyol, said polyol selected from the group consisting of glycerol; sorbitol, propylene glycol, butylene glycol, xylitol, cyclodextrin and its derivatives, and mixtures thereof;

d) about 0.01 weight % to about 10 weight % of an orally acceptable surfactant; and e) an orally acceptable carrier, wherein the unpleasant taste of the phenolic is masked by the citrus flavor, citrus flavor ingredient, or mixtures thereof as the essential phenolic taste masking agent to act as an antagonist to phenolic taste receptors on the tongue, said composition being low temperature stable and substantially clear and substantially free of preceipitants, flocculants, or crystals at about room temperature.

12. The composition of claim 11, wherein said citrus flavor is selected from the group consisting of orange, grapefruit, lemon, mandarin orange, lime, tangerine, and tangelo; and said citrus flavor ingredient is selected from the group consisting of limonene, citral, cadiene, decylaldehyde, linalool, terpineol, linalyl esters, terpinyl acetate, citronellal, α-terpinene, γ-terpinene, 2-dodecanal, α-pinene, β-pinene, 2-pentenal, decanal, and $C_8$ to $C_{10}$ and $C_{12}$ aldehydes, acids, and esters found in citrus flavors.

13. The composition of claim 11, wherein said citrus flavor, citrus flavor ingredient, or mixtures thereof includes limonene.

14. The composition of claim 13, wherein the ratio of said limonene to said phenolic is at least about 0.05:1.

15. An oral gel composition comprising:

a) about 0.01 weight % to about 5 weight % of citrus flavor selected from the group consisting of orange, grapefruit, lemon, mandarin orange, lime, tangerine, and tangelo; citrus flavor ingredient selected from the group consisting of limonene, citral, cadiene, decylaldehyde, linalool, terpineol, linalyl esters, terpinyl acetate, citronellal, a-terpinene, γ-terpinene, 2-dodecanal, α-pinene, β-pinene, 2-pentenal, decanal, and $C_8$ to $C_{10}$ and $C_{12}$ aldehydes, acids, and esters found in citrus flavors, and mixtures thereof;

b) about 0.01 weight % to about 5 weight % of a phenolic, said phenolic selected from the group consisting of menthol, eucalyptol, methyl salicylate, thymol, and mixtures thereof;

c) about 0.1 weight % to about 70 weight % of a polyol, said polyol selected from the group consisting of glycerol, sorbitol, propylene glycol, butylene glycol, xylitol, cyclodextrin and its derivatives, and mixtures thereof;

d) about 0.01 weight % to about 10 weight % of an orally acceptable surfactant; and e) an orally acceptable carrier, wherein the unpleasant taste of the phenolic is masked by the citrus flavor, citrus flavor ingredient, or mixtures thereof as the essential phenolic taste masking agent to act as an antagonist to phenolic taste receptors on the tongue said composition being low temperature stable and substantially clear and substantially free of precipitants, flocculants, or crystals at about room temperature.

16. The composition of claim 15, wherein said citrus flavor, citrus flavor ingredient, or mixtures thereof includes limonene.

17. The composition of claim 15, wherein the ratio of said limonene to said phenolic is at least about 0.05:1.

18. A method for retarding development of plaque on a dental surface in the oral cavity of a mammal, comprising administering to said dental surface an amount of a composition according to claim 1 effective in retarding said development of plaque.

19. A method of treating gingivitis, comprising administering to a mammal in need of such treatment an amount of a composition according to claim 1 effective in treating gingivitis.

20. A method of treating the presence of micro-organisms in the oral cavity of a mammal, comprising administering to the mammal in need of such treatment an amount of a composition according to claim 1 effective in reducing the viable population of said micro-organisms.

* * * * *